United States Patent [19]
Thut et al.

[11] Patent Number: 6,153,221
[45] Date of Patent: Nov. 28, 2000

[54] USE OF BIOGICALLY ACTIVE GLASS AS A DRUG DELIVERY SYSTEM

[75] Inventors: Paul D. Thut, 6309 Blenheim Rd., Baltimore, Md. 21212; Leonard J. Litkowski, 621 Sussex Rd., Towson, Md. 21286; David C. Greenspan, Gainesville, Fla.

[73] Assignees: Paul D. Thut, Baltimore; Leonard J. Litkowski, Towson, both of Md.

[21] Appl. No.: 09/157,636

[22] Filed: Sep. 21, 1998

Related U.S. Application Data

[62] Division of application No. 08/940,393, Oct. 1, 1997, Pat. No. 5,972,384.

[51] Int. Cl.$^7$ .............................. A61K 9/10; A61K 9/14
[52] U.S. Cl. ............................................ 424/484; 424/423
[58] Field of Search ..................................... 424/400, 423, 424/489, 486, 484; 514/951, 953, 964–65, 769–770

[56] References Cited

U.S. PATENT DOCUMENTS

| | | |
|---|---|---|
| 4,103,002 | 7/1978 | Hench et al. . |
| 4,138,325 | 2/1980 | Barrett et al. . |
| 4,159,358 | 6/1979 | Hench et al. . |
| 4,171,544 | 10/1979 | Hench et al. . |
| 4,218,255 | 8/1980 | Bajpai et al. . |
| 4,234,972 | 11/1980 | Hench et al. . |
| 4,775,646 | 10/1988 | Hench et al. . |
| 4,851,046 | 7/1989 | Low et al. . |
| 5,074,916 | 12/1991 | Hench et al. . |
| 5,262,166 | 11/1993 | Liu et al. . |
| 5,294,446 | 3/1994 | Schlameus et al. . |
| 5,591,453 | 1/1997 | Ducheyne et al. . |
| 5,626,861 | 5/1997 | Laurencin et al. . |
| 5,643,789 | 7/1997 | Ducheyne et al. . |
| 5,648,301 | 7/1997 | Ducheyne et al. . |

FOREIGN PATENT DOCUMENTS

| | | |
|---|---|---|
| US95/09401 | 7/1995 | WIPO . |

OTHER PUBLICATIONS

Hench, L. L. et al., "Direct chemical Bond of Bioactive Glass–Ceramic Materials to Bone and Muscle." *J. Biomed. Mater. Res. Sym.*, No. 4, p. 25–42 (1973).

Hench, L. L. et al., "Bonding Mechanisms at the Interface of Ceramic Prosthetic Materials." *J. Biomed. Mater. Res. Sym.*, No. 2 (part 1) p.117–141 (1971).

Wilson, J. et al., "Biomaterials for facial bone augmentation: Comparative studies." *J. Biomed. Mate. Res.*, vol. 22, No. A2, p159–177 (1988).

Wilson, J. et al., "Toxicology and biocompatibility of bioglasses." *J. Biomed. Mater. Res.*, vol. 15, p805–817 (1981).

Bentia, S., "Microencapsulation: Methods and Industrial Application." *Marcel Dekker, Inc.*, 1996.

Otsuka, M., et al., "New Skeletal Drug Delivery system Containing Antibiotics Using Self–Setting Bioactive Glass Cement", *Chem. Pharm. Bull.*, 40(12): 3346–3348, 1992.

Otsuka, M., et al., "A Novel Skeletal Drug Delivery System for Antibiotic Drugs using Self–Setting Bioactive Bone Cement Based on $CaO–SiO_2–P_2O_5$ Glass", *Bioceramics*, 5: 241–248, 1992.

Wilson, J., et al., "Bioactive Materials For Periodontal Treatment: A Comparative Study", *Biomaterials and Clinical Application*, 223–228, 1987.

*Primary Examiner*—Edward J. Webman
*Attorney, Agent, or Firm*—Burns, Doane, Swecker & Mathis, L.L.P.

[57] ABSTRACT

This invention relates to a synthetic bone replacement material impregnated with drugs such as antibiotics and growth hormones, which facilitate and promote the regeneration of bone and/or soft tissue. Methods for making the impregnated material and its medical use are also taught.

7 Claims, 6 Drawing Sheets

USE OF BIOGICALLY ACTIVE GLASS AS A DRUG DELIVERY SYSTEM

This application is a divisional of application Ser. No. 08/940,393, filed Oct. 1, 1997 now U.S. Pat. No. 5,972,384.

The present invention relates to a particulate, biologically active ceramic-glass material in conjunction with one or more therapeutically beneficial micro-encapsulated drugs and its use as a means for the controlled delivery of the drugs into the body of a mammal in need thereof.

BACKGROUND OF THE INVENTION

A drug may be administered to a patient systemically or locally. When a drug is administered systemically, it enters the circulatory system, i.e., the blood stream, travels throughout the body, and hopefully, an effective amount of the drug will reach the part of the patient's body in need of treatment before the drug is degraded by metabolism and excreted. Typically, a drug is taken orally in the form of a syrup, tablet, capsule and the like, passes through the stomach then into the intestines where it passes through the intestine walls into the blood stream. Alternatively, the drug may be injected directly into the blood stream or into soft tissue where it diffuses into the blood stream.

In recent years, drugs have also been administered systemically by transdermal delivery. That is, the drug is placed on the skin (typically the drug is incorporated into a patch) and allowed to diffuse through the skin to enter the blood stream. In a variation of this form of administration, a drug formulation in a metabolizable matrix or a container is implanted under the skin where the drug is slowly released and finds its way into the patient's blood stream. This form of drug delivery is particularly advantageous when a continuous, constant, low level of drug is desirable. For example, this method is currently being used to administer small amounts of nicotine to help patients stop smoking, and to deliver a birth control drug over several weeks.

Topical administration is the most common form of local drug delivery. Typically a drug containing formulation is placed directly on the area of the body needing the drug. For example, an antibiotic in the form of a cream or ointment may be spread onto an injured area of the skin, or a drug in the form of an aerosol may be sprayed onto an inflamed mucus membrane. Drugs may also be locally administered by injection. For example, a dentist may inject an anesthetic into a patient's gums to deaden the pain of a tooth extraction.

Often systemic delivery of a drug is inefficient because only a small amount of the administered dose reaches its site of therapeutic action. In many cases, especially where the toxicity of the drug is low, this inefficiency may be off set by giving the patient a large enough dose of the drug to compensate for its loss while it travels through the patient's body. In some cases, local drug delivery is very difficult, if not impossible, leaving systemic administration as the only viable alternative. For example, if the patient is in need of an antipsychotic drug, injection directly into the brain would not be considered. Perhaps the biggest problem with systemic delivery is that a drug can enter parts of the body where it can actually do harm or produce a noxious side effect.

Since the early days of modern medicine, physicians have sought to replace damaged bone tissue with an artificial material. In many cases the goal has been not merely to replace the bone with a prothesis, but to provide a matrix upon which new bone tissue could grow. Of course, such a replacement material must be essentially nontoxic and nonallergenic, relatively stable in physiologic environments, and mechanically strong, but it should also bind to living tissue. Many polymeric and noble metal materials have been used as bone replacement materials with limited success rates. Generally, living tissue does not bind well, if at all, with these relatively inert materials, which has limited their successful use.

In recent years, more biologically active, "bioactive," materials have been developed to which living bone tissue binds well. In particular, certain inorganic, that is, ceramic, glass and ceramic-glass, materials with relatively high bioactivity are now available. These inorganic materials can be made with a porous structure which supports new bone tissue. Ideally, the living tissue grows on and into the replacement material to ultimately incorporate the material into a new bone structure. See U.S. Pat. Nos. 4,159,358; 4,234,972; 4,103,002; 4,189,325; 34,171,544; 4,775,646; 4,857,046; and 5,074,916 (all incorporated herein by reference) for information on ceramic-glass bioactive materials.

These bioactive materials have been shown to develop a strong bond with hard tissue because of a series of ion exchange reactions between the implant surface and body fluids that result in the formation of a biologically active calcium phosphate film at the implant tissue interface. See Hench et al, *J. Biomed. Mater. Res.*, Vol. 5, pp. 117–141 (1971), and Hench et al, *J. Biomed. Mater. Res.*, Vol. 7, pp. 25–42 (1973). Bio-active glasses have also been shown to form firm bonds with soft tissue. See Wilson, et al, *J. Biomed. Mater. Res.*, Vol. 15, pp. 805–817 (1981); Wilson and Merwin, *J. Biomed. Mater. Res.: Applied Biomaterials*, Vol. 22, No. A2, pp. 159–177 (1988); and Wilson, Low et al, *Biomaterials and Clinical Applications*, Ed. By Pizzoferrato et al, Elsevier Science Publishers B.V., Amsterdam (1987). Many of these inorganic materials are biodegraded at a slow rate, so that in time, the replacement material disappears leaving natural bone structure in its place.

In conjunction with implantation of biologically active materials, parenteral or oral administration of beneficial drugs, e.g., antibiotics, hormones, and hormone-like material, have been demonstrated to enhance formation of new bone and to prevent infection, with varying degrees of success. However, the systemic delivery of such drugs results in distribution of the drugs to sites where their effects are not required and where they may do harm. Further, local administration has been difficult and not practical.

The physical mixing of antibiotic drugs either in free drug form (Otsuka, et al. *Bioceramics*, 5, 241 (1992)) or in the form of pulverized binder containing antibiotic tablets with the bone substitute, results in uneven biological activity and nonuniform release (Otsuka, et al. *Chem. Pharm. Bull.*, 40, 3346 (1992)). In particular, in cases where a drug has been uniformly mixed with ceramic-glass and implanted to form a matrix onto which new bone can grow (for example see, U.S. Pat. No. 5,591,453), the concentration of the drug rapidly rises to a therapeutic range. Unfortunately, the concentration of the drug continues to rise, exceeding the therapeutic range and entering the potentially toxic range. As metabolism and diffusion take effect, the concentration of the drug drops back into the therapeutic range but continues to drop. The concentration of the drug rapidly becomes sub-optimal and its therapeutic benefit is lost. Although there are no reports of a hormone being mixed directly with ceramic glass in lieu of an antibiotic drug, it is logical that the changes in hormone level would follow a similar pattern.

The object of the present invention is to provide a particulate, biologically active ceramic-glass impregnated with one or more therapeutically beneficial drugs in a microencapsulated form and capable of releasing the drugs at a controlled, predetermined rate. The ceramic-glass may act as a bone substitute or a depot for the therapeutically beneficial drugs to be released for systemic or local treatment.

SUMMARY OF THE INVENTION

An aspect of the present invention is a particulate, biologically active, ceramic-glass material in conjunction with one or more microencapsulated therapeutically beneficial drugs, capable of releasing the drugs at a predetermined rate when placed in a physiological environment, either in bone or soft tissue. This impregnated biologically active, ceramic-glass material is referred to as "ceramodrug matrix".

A second aspect of the present invention is a method for preparing the ceramodrug matrix of the first aspect comprising the following sequential steps:
a) Forming one or more drugs into biodegradable micro capsules which degrade in physiological fluids at a pH level higher than about 7,
b) Forming a colloidal suspension of the biologically active, ceramic-glass material by mixing the finely divided biologically active, ceramic-glass material in one or more solvents, optionally void of suspending agent,
c) Stirring the micro capsules prepared in step a with the colloidal suspension prepared in step b to yield a cosuspension of micro capsules of drug and the biologically active, ceramic-glass, and
d) Removing the solvent in a sequential manner from the suspension formed in step c yielding a ceramodrug matrix.

A third aspect of the present invention is a method for promoting the regeneration of missing or damaged bone tissue in a mammal comprising replacing the missing or damaged bone tissue with ceramic-glass bone replacement material, impregnated with at least one therapeutically beneficial drug in microencapsulated form, capable of releasing the drug at a predetermined rate when placed in a physiological environment.

A fourth aspect of the present invention is a method for the controlled release of therapeutically beneficial drugs into the bone or soft tissue of a mammal in need of such drugs by placing ceramic-glass material, impregnated with at least one therapeutically beneficial drug in microencapsulated form, capable of releasing the drug at a predetermined rate when placed in a physiological environment into the bone or soft tissue of the mammal.

BRIEF DESCRIPTION OF THE DRAWINGS

FIG. 4b is a graph showing tissue concentration of multiple drugs released by a ceramodrug matrix as a function of time where each drug in the ceramodrug matrix is microencapsulated, according to the diagram of FIG. 4a.

DETAILED DESCRIPTION OF THE INVENTION

As used herein the term "drug" has its usual meaning and includes, but is not limited to, analgesics, local anesthetics, antibiotics, steroids, anti-tumor agents, hormones, and hormone-like agents. "Bone replacement material" is a substance that fills space left when bone is remove by injury or surgery, which aids in forming an adhesion between adjacent healthy bone and which is replaced by osteoblasts during the bone healing and remodeling process, and, as used herein, is synonymous with "bone matrix material." The terms "biologically active ceramic," "biologically active glass," and "biologically active ceramic-glass" refer to inorganic material containing an oxide of silicon as the predominate component which is altered slowly by tissue fluids and which is remodeled during formation of new bone.

As used herein the terms "microencapsulate" and "micro capsules" refer to solid, colloidal, or liquid drug contained within a coating of a material which dissolves or degrades in a physiological environment. The micro capsules taught herein have a size greater than about 10 $\mu$M and less than about 1000 $\mu$M. The term "micro spheres" as used herein means a form of micro capsules of approximate sphere-shaped particles of a solid matrix into which is embedded drug substances.

As used herein the term "ceramodrug matrix" means a composition comprising particles, micro capsules, or microspheres of one or more drugs distributed among the particles of the biologically active, ceramic-glasses.

Figure 1:
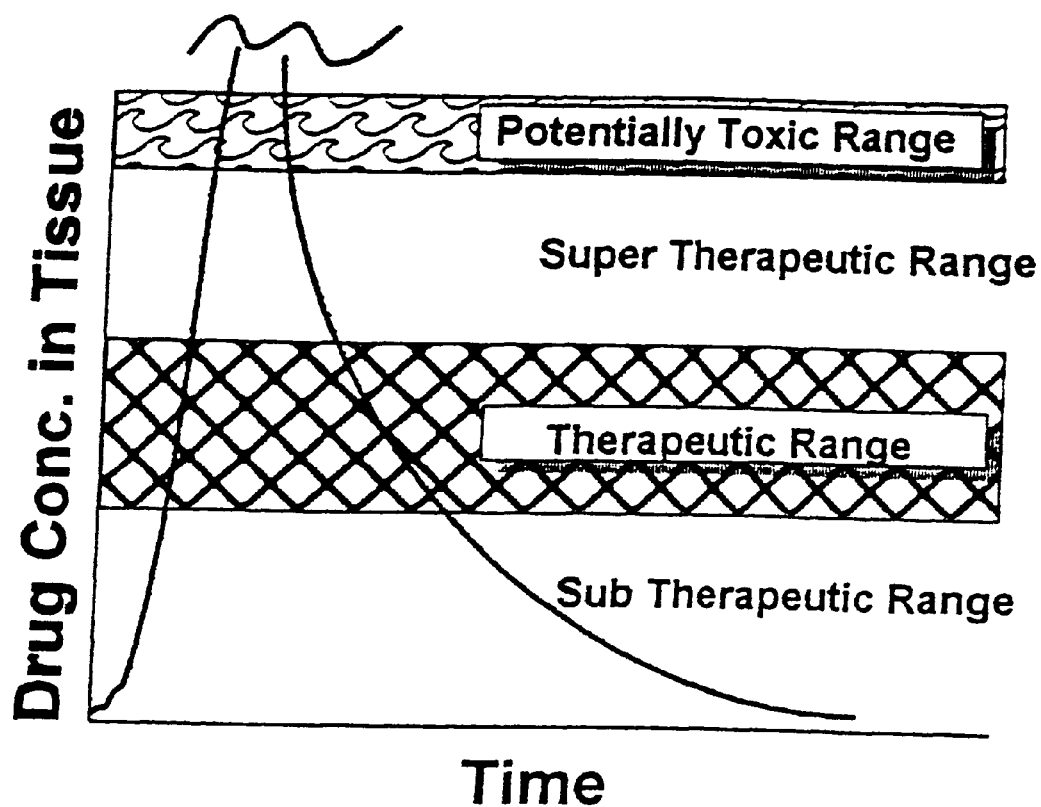
FIG. 1 is a graph showing the dramatic variation in the tissue concentration of drug released by a ceramodrug matrix as a function of time where the drug is simply mechanically mixed with a biologically active, ceramic-glass.

Referring to the graph of FIG. 1, if a finely divided drug intimately mixed with a finely divided biologically active, ceramic-glass to form a ceramodrug matrix is placed in bone or soft tissue, the concentration of the drug in the surrounding tissue rapidly rises as biologic fluids dissolve and distribute the drug as a function of time. The concentration quickly reaches the therapeutic range (cross hatched area in FIG. 1) and continues to rise through the super therapeutic range and into the potentially toxic range. As the body metabolizes the drug, the level drops over a short time, passing back through the therapeutic range, but quickly entering the ineffective sub therapeutic range. This profile of drug delivery might be used where it is important to deliver a burst of drug over a short period. However, this profile would not generally be preferred, and for some drugs a sudden, high concentration could be toxic to the tissue.

Figure 2:
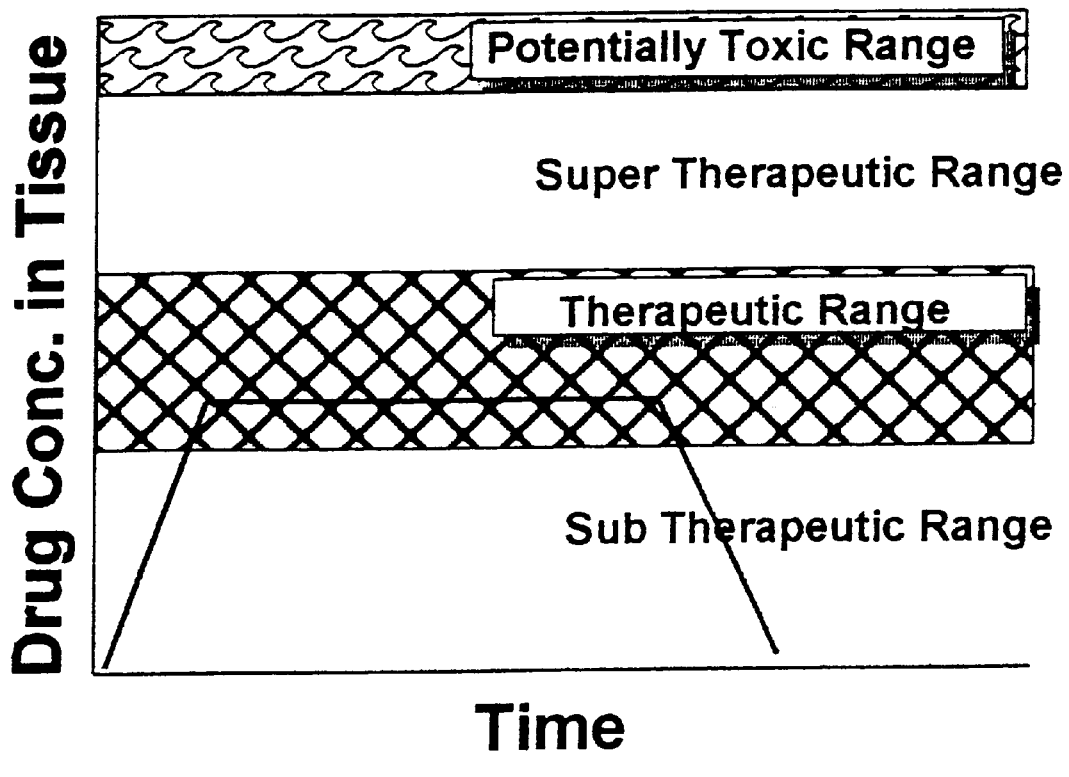
FIG. 2 is a graph showing tissue concentration of drug released by a ceramodrug matrix as a function of time where the drug is adsorbed onto ceramic-glass.

FIG. 2 illustrates the preferred delivery profile for most drugs. The concentration in the surrounding tissue rapidly rises to a level within the therapeutic range and that level is maintained until all the drug in the depot has been delivered. One means to achieve this profile, is to adsorb the drug onto a divided particulate, ceramic-glass matrix. As the surface region of the mixture becomes progressively moistened with biological fluid, successive molecules of drug are "de-adsorbed" to maintain an effective therapeutic concentration of the drug in the surrounding tissue over an extended period. Unfortunately, predictable adsorption and de-adsorption are only practical if the matrix material is biologically inert which significantly limits the utility of the matrix itself. That is, the biologically active, ceramic-glass, which is preferred for bone replacement, does not readily adsorb drugs. Further, when an insoluble biologically inert material to which drug is absorbed is implanted in soft tissue, the material is likely to be encapsulated by tissue to form a cyst.

Biodegradable micro capsules, containing soluble drug or hormone material, can be prepared which will release material at a constant rate over measured periods of time. This can be achieved using the property of biologically active, ceramic-glass to form a slightly alkaline interface at its exposed surface as apatite is formed. Within the biologically active ceramic-glass matrix, wetting with biological fluids will occur but the pH will not change. Microcapsule formulations which are stable at pH levels below about 8 or 9 and which lyse or release at pH above about 9 are preferred. Drug release is controlled at, and limited to, the site where apatite is being formed.

Figure 3A:
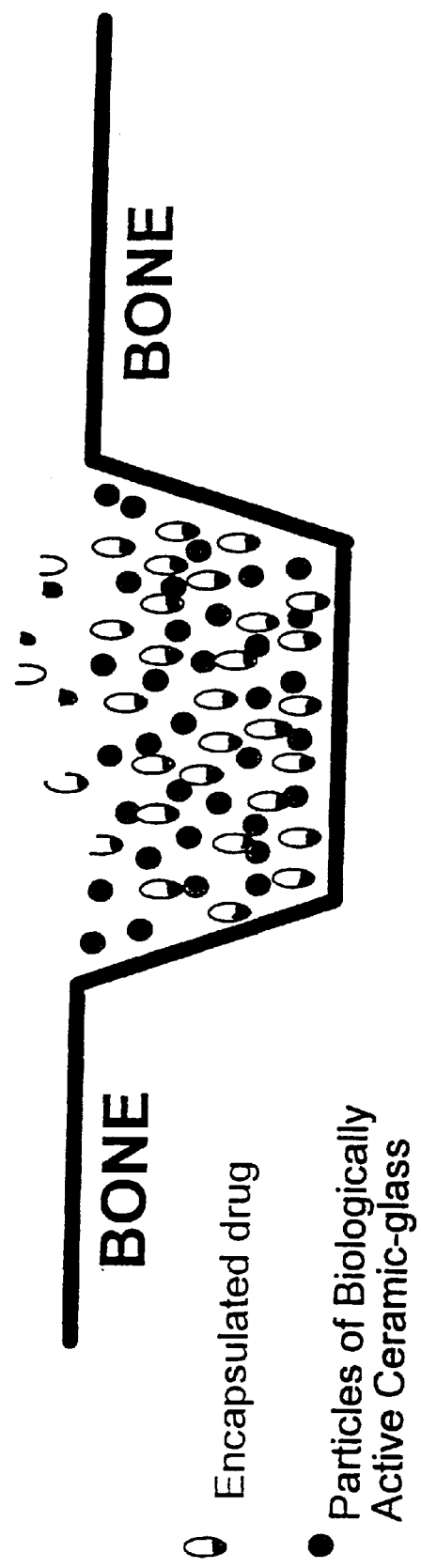
FIG. 3a is a schematic diagram showing a microencapsulated drug in a ceramodrug matrix filling a cavity within a bone, such that only the surface is exposed to biological fluids.

FIG. 3a schematically illustrates the material of the present invention wherein one or more drugs are microencapsulated and the micro capsules are intimately mixed with finely divided particulate, biologically active ceramic-glass. Upon placement in a biological environment, e.g., in bone or soft tissue of a patient, exposure to the biological fluids ruptures the micro capsules to release the drug into the surrounding tissue. Exposure and rupture of the micro capsules occurs only at the surface of the matrix.

Figure 3B:
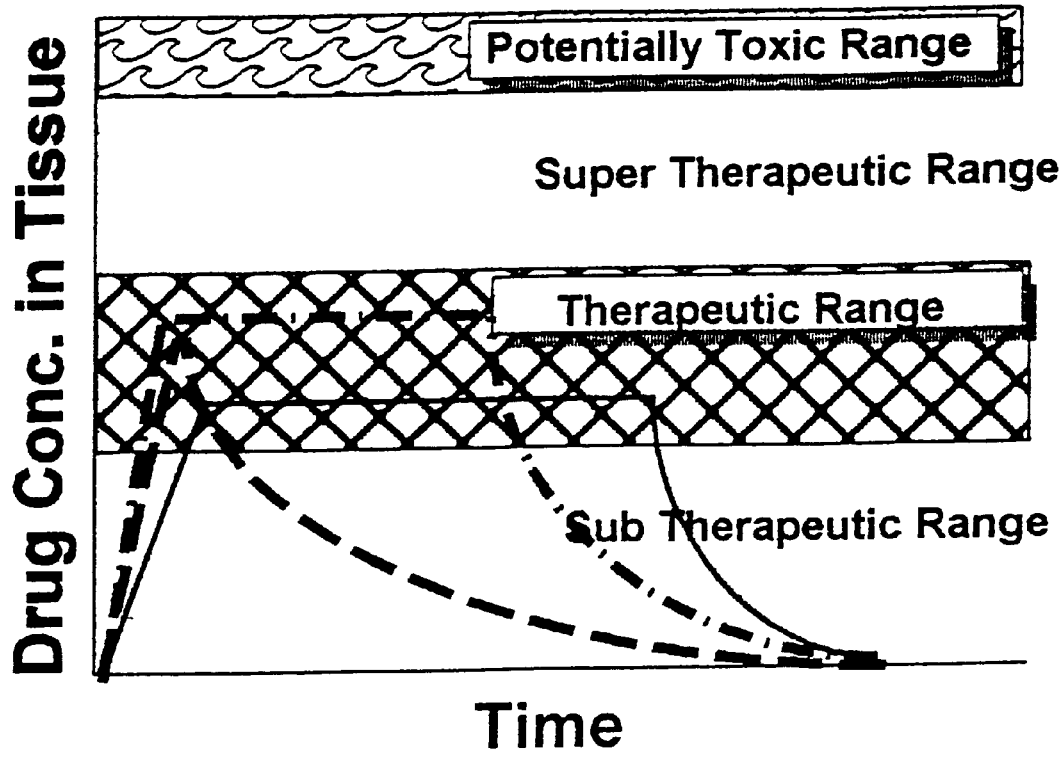
FIG. 3b is a graph showing three variations of tissue concentration of a drug released by a ceramodrug matrix as a function of time where the drug is microencapsulated and distributed among the particles of the biologically active, ceramic-glass matrix but certain conditions are varied.

Referring to the graph in FIG. 3b, because the rate of release of drug is proportional to the surface area, maintaining a constant surface area leads to a constant rate of drug release and generally preferred drug delivery profile illustrated by the solid line. The drug release profile of the material of the present invention can be tailored to meet the preferred delivery profile of a particular drug by varying the exposed surface area and the composition/thickness of the microencapsulating material.

Still referring to the graph in FIG. 3b, if the material of the present invention were implanted into soft tissue in the form of a sphere, a drug delivery profile illustrated by the dashed line might be achieved as the sphere of uniform drug concentration continuously decreased in surface area. However, layers of the material of the present invention impregnated with varying amounts of drug could be built-up to make an implant with high drug concentration in the interior of the sphere and progressively lower concentrations in the outer shells of the sphere. Thus, as the surface area of the sphere is diminished by biological erosion, the amount of the drug released is held constant since the concentration of drug is greater in the interior of the drug delivery sphere. These drug delivery spheres would provide the stable delivery profile illustrated by the dash-dot-dash line.

Figure 4A:
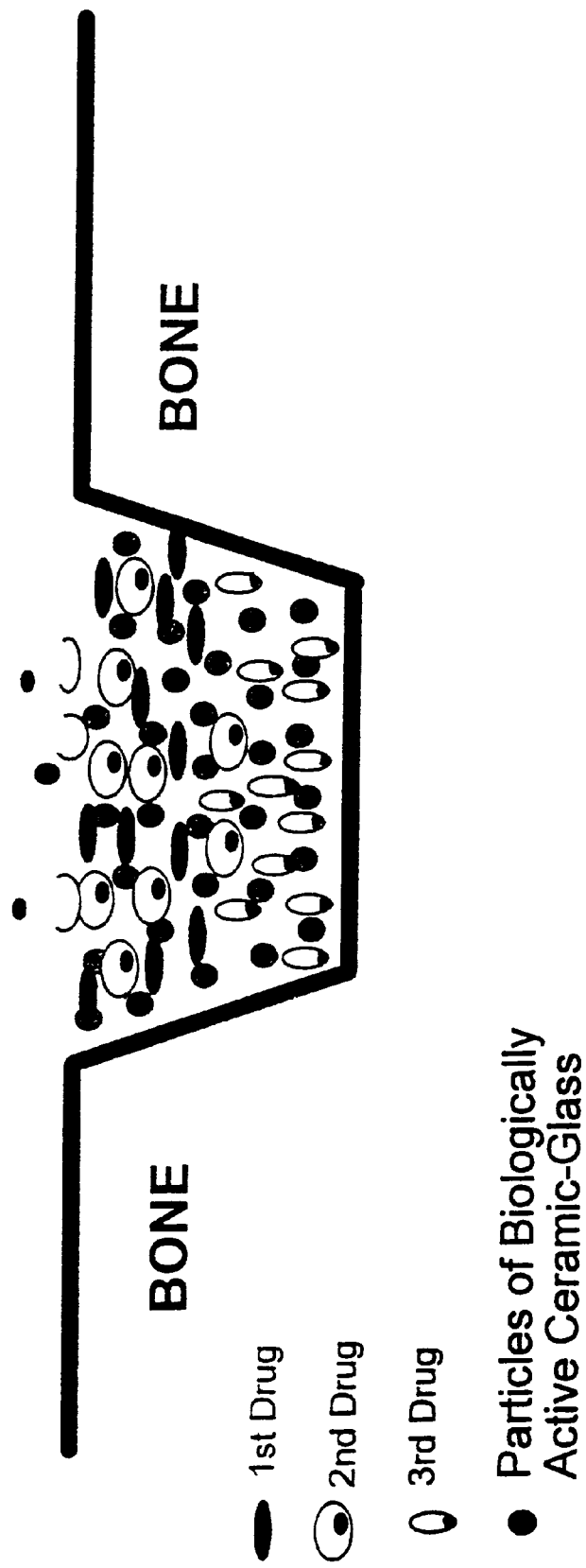
FIG. 4a is a schematic diagram similar to that of FIG. 3a but with multiple drugs distributed in a ceramodrug matrix in gradients.

Referring to the schematic diagram in FIG. 4a, by forming biologically active ceramic-glass in a colloidal block with a nonuniform distribution of microencapsulated drugs, one could regulate the concentration and biological sequencing of drugs. Conveniently, nonuniform distribution of drug in a biologically active ceramic-glass matrix is obtained by building up layers varying in drug concentration and composition as taught above. In this illustration, biologically active ceramic-glass has been combined with a microencapsulated antibiotic and analgesic and two different bone growth hormones. A higher concentration of antibiotic and analgesic micro capsules is placed near the surface of the colloid than in its interior. Thus, higher, stable analgesic and antibiotic concentrations are achieved immediately after surgery.

Figure 4B:
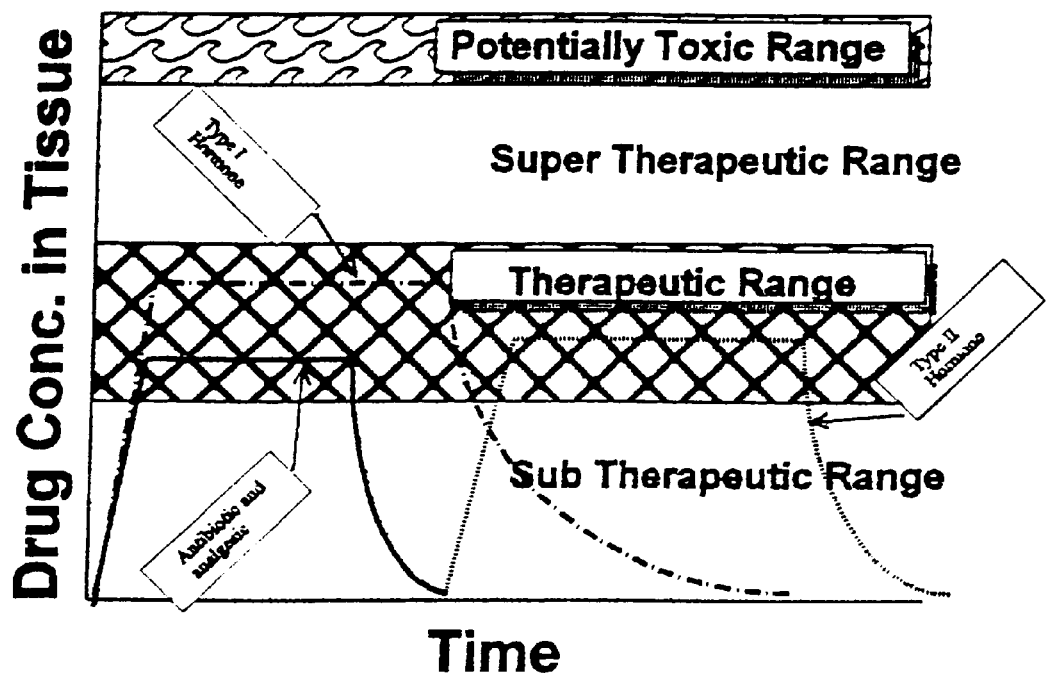

As illustrated by the graph of FIG. 4b, at an appropriate time, further local antibiotic treatment is unnecessary and the concentration of antibiotic capsules deeper in the colloid is zero. The Type I hormone is required to initiate infiltration of the matrix with osteoclasts. This enhances initial remodeling, but if left to continue, this remodeling would be counter productive. A second growth stimulating hormone (Type II) is microencapsulated at a layer farther within the colloid. As aqueous diffusion into the colloid progresses, the high pH is formed deeper within the colloid, releasing the Type II hormone to sustain the secondary phases of bone reformation.

Thus, the combination of biologically active ceramic-glass with its resultant unique pH change in the physiologic environment and biodegradable microcapsule will result in the delivery of the drug or hormone-like substances to a surgically defined site. These concentrations can be regulated to be appropriate for the local tissue requiring treatment and do not effect distal sites because systematic concentrations would be minimal. Further, the material can be sequenced. The technique is appropriate for current and future antibiotics. It is also useful for local administration of both endocrine and locally acting hormonal substances. The techniques developed will also serve as delivery methods for therapies developed through genetic engineering.

Optionally, binding agents may be added to a ceramodrug matrix to enhance its moldable qualities. A binder can be a material which becomes rigid or viscous some time after activation. For example, the binder may be a cement-like material which upon mixing with water or biological fluids "sets-ups" within a few minutes to a few hours depending on the applications.

Typically, the matrix material might be stored as finely divided particles. Just prior to application, the material would be mixed with a physiologically comparable substance, e.g., buffered, sterile water or normal saline, to form a thick paste, which would be placed in the area where the bone was to be reconstructed. Upon contact with physiological fluids, the material would become rigid or semi-rigid due to surface interactions with macromolecules.

Alternatively, the material may be supplied as preformed into semi-rigid shapes, such as strips, rods, spheres, etc., which could be molded or sculptured to the required shape by the surgeon just prior to implantation as a bone replacement material. Also, the material could be preformed into stock or custom shapes closely approximating the shapes of the bone section to be replaced.

In addition to being physiologically comparable, an acceptable binder degrades in a physiologically active environment at approximately the same rate as the rate as the biologically active ceramic-glass when it is being replaced by bone. The material of the present invention may also optionally contain preservatives, stabilizers, colorants, and buffers.

Where the drug impregnated biologically active ceramic-glass material is used solely as drug depot in soft tissue, and not also as a bone replacement material, it is preferably implanted in a rigid or semi-rigid form which maintains approximately constant surface area over most of its effective life. Alternatively, the impregnated biologically active ceramic-glass matrix material can be placed in a cavity of a solid material that degrades at a lesser rate than the biologically active ceramic-glass. For example, the impregnated biologically active ceramic-glass material might be placed in a thin wall, wide diameter open-ended cylinder where the exposed surface would be approximately constant, and consequently, the drug delivery profile would be approximately constant. The matrix material could also be implanted in the form of regular or irregular solid, geometric shapes, e.g., thin strips, spheres, spheroids, etc.

The drug impregnated biologically active ceramic-glass material of the present invention need not be homogeneous when used as a bone replacement material. For example, several formulations of matrix material of varying concentrations and combinations of drug may be added in layers within a bone cavity. Because the amount of drug delivered is directly proportional to the exposed surface of the matrix, a typical solid geometric shape, e.g., a sphere, would deliver progressively less drug as the sphere was degraded in a biological environment if it were of uniform composition. Therefore, the concentration of the drug in the matrix is a decreasing gradient moving from the center of the solid to the surface. The effect of diminished delivery because of diminished surface area can be compensated by making the interior of the solid a greater concentration than the exterior portion.

Particulate, bioactive ceramic glasses in accordance with the present invention typically have the following composition by weight percentage:

| Compound | % | Compound | % |
|---|---|---|---|
| $SiO_2$ | 40–60 | $CaF_2$ | 0–25 |
| CaO | 10–30 | $B_2O_3$ | 0–10 |
| $Na_2O$ | 10–35 | $K_2O$ | 0–8 |
| $P_2O_5$ | 2–8 | MgO | 0–5 | where the total percentage equals 100. The preferred composition of the bioactive ceramic glass is:

| Compound | % |
|---|---|
| $SiO_2$ | 45.0 |
| CaO | 24.5 |
| $Na_2O$ | 24.5 |
| $P_2O_5$ | 6.0 | which is commercially available under the trademark Bioglass® (supplied by US Biomaterials, One Progress Boulevard, #23, Alachua, Fla., 32615)

The particulate biologically active material used in the present invention may be prepared according to the methods of the art such as taught in U.S. Pat. Nos. 4,159,358; 4,234,972; 4,103,002; 4,189,325; 134,171,544; 4,775,646; 4,857,046, and 5,074,916. For example, the raw materials (e.g., $SiO_2$, CaO, $Na_2O$ and $P_2O_5$) are mixed in a Nalgene (trademark) plastic container on a ball mill for four hours. The mix is then melted in a platinum crucible at 1350° C. and homogenized for 24 hours. The molten glass is poured into distilled, deionized water to produce a glass frit. The frit is ground in a mortar and pestle and passed through ASTM sieves to produce the required particle size range.

The preferred particle size range for the bioactive glass is site and use dependent. Particle sizes less than about 1000 microns and greater than about 2 microns can also be used. Particles of such a small size range generally provide for the advantages of the present invention but do not elicit any undesirable immune response.

Examples of antibiotics useful with the present invention include, but are not limited to: ampicillin, chloramphenicol, chlortetracycline, clindamycin, erythromycin, gramicidin, gentamicin, mupiroicin, neomycin, polymyxin B, bacitracin, silver sulfadiazine, tetracycline and chlortetracycline. Those of ordinary skill in the art will appreciate that there are other appropriate topical antibiotics, such as those listed in U.S.P.D., which may also be used in the present invention.

Examples of hormones and other related drugs useful with the present invention include, but are not limited to: human growth hormone (hGH), bone morphogenetic proteins (BMPs) (C.F. Paatsama, S., et al.) transforming growth factors (TGF-βs), interferons, interleukins, calcitonin, estrogen and 17-β estradiols. Examples of anti-inflammatory drugs include, but are not limited to: cortisone, Nonsteroidal Anti-inflammatory Drugs (NSAIDs), and interleukin 3 inhibitors.

A drug may be microencapsulated and mixed with particulate bone matrix material. This technique is useful for both biologically inert and biologically active matrix materials. Biodegradable micro capsules, containing one or more drugs can be prepared by methods known in the art (see *Microencapsulation: Methods and Industrial Application*, ed. by Simon Benita, Marcel Dekker, Inc. New York, 1996). Particularly useful are microcapsule formulations which are stable at pH levels below about 9 and which lyse or release at pH above about 9. By controlling these pH variations, drug release will be controlled at and limited to the site where apatite is being formed.

The ceramodrug matrix of the present invention is useful in repairing bone defects which have been caused by surgical removal due to cancer, lost bone due to infection or trauma, or lengthening or remodeling of bone underlying soft tissue. Specific examples include repairing trephine holes remaining after neurosurgery, bone grafting in periodontal and maxillofacial surgery and repair of long bones which have been chipped or shattered as a result of trauma.

Many of the antitumor drugs in current clinical use are cytotoxic materials which work by killing the malignant cells faster than the normal cells. When these potent drugs are given systemically, a large number of normal cells are killed or disabled which often leads to massive, undesirable side effects. It has long been recognized that localized tumors could best be treated by delivering a small, but effective, amount of an appropriate drug close to or, even better, inside the tumor. Preferably, an antitumor drug, or mixture of drugs, would be delivered directly to the tumor site to form a high drug concentration in the immediate vicinity of the tumor with minimal amount reaching the blood stream and being carried throughout the body. Ideally, the drug would be delivered in a controlled manner over a period of time.

The ceramodrug matrix of the present invention is well suited for localized treatment of tumors. The biologically active ceramodrug matrix impregnated with one or more antitumor drugs can be injected directly into the tumor or implanted in close proximity to the tumor. The material of the present invention is especially suited for treatment of malignancies of the bone.

The material of the present invention can be formulated to deliver drugs systematically where such a mode of delivery is advantageous to the patient. For example, the ceramodrug matrix may be impregnated with a high concentration of microencapsulated drug and the drug can be microencapsulated by a material that is easily lysed. Further, the impregnated material can be placed in tissue rich in blood vessels. A low level, continuous, predictable, systematic delivery method is useful for hormone replacement therapy, as well as for birth control, and delivery of antidepressant, antipsychotic and anticonvulsant drugs.

What is claimed is:

1. A method for promoting the regeneration of missing or damaged bone tissue in a mammal comprising replacing the missing or damaged bone tissue with biologically active, ceramic-glass material impregnated with at least one beneficial, physiologically active drug in microencapsulated form, capable of releasing the agent at a predetermined rate when placed in a physiological environment.

2. The method of claim 1 wherein the beneficial drug is selected from the group consisting of antibiotics, analgesics, local anesthetics, 17-β estradiols, bone morphogenetic proteins, anti-epileptics, endocrine hormones, cytokines, interleukins leukotrienes, calcitonin, transforming growth factors-β, interferons, corticols, non-steroidal anti-inflammatory drugs, interlukins 3 inhibitors and growth hormones.

3. The method of claim 1 wherein the beneficial drug is one or more antibiotics and one or more growth hormones.

4. The method of claim 1 wherein the beneficial drug is microencapsulated as microspheres.

5. The method of claim 1 wherein the biologically active, ceramic-glass material has the following composition of component compounds:

| Compound | % | Compound | % |
| --- | --- | --- | --- |
| $SiO_2$ | 40–60 | $CaF_2$ | 0–25 |
| CaO | 10–30 | $B_2O_3$ | 0–10 |
| $Na_2O$ | 10–35 | $K_2O$ | 0–8 |
| $P_2O_5$ | 2–8 | MgO | 0–5 | with the proviso that the sum of the percentage of the component compounds equals 100%.

6. The method of claim 5 wherein the biologically active ceramic-glass material has the following composition of component compounds:

| Compound | % |
| --- | --- |
| $SiO_2$ | 45.0 |
| CaO | 24.5 |
| $Na_2O$ | 24.5 |
| $P_2O_5$ | 6.0. |

7. The method of claim 1 wherein the predetermined rate is substantially a uniform rate.

* * * * *